(12) United States Patent
Christian et al.

(10) Patent No.: US 6,783,943 B2
(45) Date of Patent: Aug. 31, 2004

(54) ROLLING CIRCLE AMPLIFICATION DETECTION OF RNA AND DNA

(75) Inventors: Allen T. Christian, Tracy, CA (US); Melissa S. Pattee, Livermore, CA (US); Cristina M. Attix, Livermore, CA (US); James D. Tucker, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 104 days.

(21) Appl. No.: 10/032,017

(22) Filed: Dec. 18, 2001

(65) Prior Publication Data

US 2002/0177142 A1 Nov. 28, 2002

Related U.S. Application Data

(60) Provisional application No. 60/257,216, filed on Dec. 20, 2000.

(51) Int. Cl.[7] ............................ C12Q 1/68; C12P 19/34; C12N 5/00
(52) U.S. Cl. ....................... 435/6; 435/91.2; 435/91.51; 435/401; 435/410
(58) Field of Search ........................ 435/6, 91.2, 91.51, 435/401, 410

(56) References Cited

U.S. PATENT DOCUMENTS

| | | | | |
|---|---|---|---|---|
| 4,889,799 A | * | 12/1989 | Henikoff et al. | ............... 435/6 |
| 5,538,871 A | * | 7/1996 | Nuovo et al. | ............... 435/91.2 |
| 5,854,033 A | * | 12/1998 | Lizardi | ............... 435/91.2 |
| 6,255,082 B1 | * | 7/2001 | Lizardi | ............... 435/91.1 |

OTHER PUBLICATIONS

Allen T. Christian, Detection of DNA point mutations and mRNA expression levels by rolling circle amplification in individual cells, PNAS Dec. 4, 2001, vol. 98, No. 25 XP-002226709.

James D. Tucker et al, Symposium "Molecular cytogenetic approach to gene mapping and function", Mutation Research 483 (Suppl. 1) (2001) S1–S192 XP-001133721.

Allen T. Christian, Rolling Circle Amplification used to detect single–base changes and gene expression levels in single cells, XP-008012365.

* cited by examiner

Primary Examiner—Kenneth R. Horlick
Assistant Examiner—Joyce Tung
(74) Attorney, Agent, or Firm—Ann M. Lee; Alan H. Thompson; Eddie E. Scott

(57) ABSTRACT

Rolling circle amplification (RCA) has been useful for detecting point mutations in isolated nucleic acids, but its application in cytological preparations has been problematic. By pretreating cells with a combination of restriction enzymes and exonucleases, we demonstrate RCA in solution and in situ to detect gene copy number and single base mutations. It can also detect and quantify transcribed RNA in individual cells, making it a versatile tool for cell-based assays.

35 Claims, 5 Drawing Sheets

SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
taatacgact cactataggg                                              20

<210> SEQ ID NO 2
<211> LENGTH: 18
<212> TYPE: DNA
<213> ORGANISM: Artificial Sequence
<220> FEATURE:

<223> OTHER INFORMATION: Synthetic Construct

<400> SEQUENCE: 2
atttaggtga cactatag                                                                  18

<210> SEQ ID NO 3
<211> LENGTH: 93
<212> TYPE: DNA
<213> ORGANISM: Artificial Sequence
<220> FEATURE:
<223> OTHER INFORMATION: Synthetic Construct

<400> SEQUENCE: 3
gttcatgccg ccctttttttt ttatttaggt gacactatag ttttttttcc ctatagtgag      60
tcgtattatt ttttttggtg aggatgggcc tct                                   93

<210> SEQ ID NO 4
<211> LENGTH: 17
<212> TYPE: DNA
<213> ORGANISM: Artificial Sequence
<220> FEATURE:
<223> OTHER INFORMATION: Synthetic Construct

<400> SEQUENCE: 4
attaaccctc actaaag                                                     17

<210> SEQ ID NO 5
<211> LENGTH: 94
<212> TYPE: DNA
<213> ORGANISM: Artificial Sequence
<220> FEATURE:
<223> OTHER INFORMATION: Synthetic Construct

<400> SEQUENCE: 5
ggttcatgcc gcccttttttt tattaaccct cactaaaggg attttttttc cctatagtga      60
gtcgtattat ttttttttggt gaggatgggc ctcc                                 94

<210> SEQ ID NO 6
<211> LENGTH: 94
<212> TYPE: DNA
<213> ORGANISM: Artificial Sequence
<220> FEATURE:
<223> OTHER INFORMATION: Synthetic Construct

<400> SEQUENCE: 6
cggttcatgc cgccctttttt ttttccctat agtgagtcgt attattttttt tagggaaatc     60 actcccaatt atttttttgg tgaggatggg cctc                                  94

<210> SEQ ID NO 7
<211> LENGTH: 94
<212> TYPE: DNA
<213> ORGANISM: Artificial Sequence
<220> FEATURE:
<223> OTHER INFORMATION: Synthetic Construct

<400> SEQUENCE: 7
tgtgagagct gcacattttt tttccctata gtgagtccta ttattttttt tttatttagg      60
tgacactata gttttttttta tctgggcctg aatc                                 94

<210> SEQ ID NO 8
<211> LENGTH: 94
<212> TYPE: DNA
<213> ORGANISM: Artificial Sequence

```
-continued

<220> FEATURE:
<223> OTHER INFORMATION: Synthetic Construct

<400> SEQUENCE: 8
cattcttctt ggcgattttt tttccctata gtgagtccta ttatttttt ttattaaccc      60 tcactaaagg gattttttt ctctaagggg atgc                                   94

<210> SEQ ID NO 9
<211> LENGTH: 98
<212> TYPE: DNA
<213> ORGANISM: Artificial Sequence
<220> FEATURE:
<223> OTHER INFORMATION: Synthetic Construct

<400> SEQUENCE: 9
gaattgaacc accgtatttt ttccctatag tgagtgagtc gtattatttt ttaaatatca      60
tctttggtgt ttcctatttt tttgtactca cactaaga                              98

<210> SEQ ID NO 10
<211> LENGTH: 94
<212> TYPE: DNA
<213> ORGANISM: Artificial Sequence
<220> FEATURE:
<223> OTHER INFORMATION: Synthetic Construct

<400> SEQUENCE: 10
gctactagct ccatttttt tttccctata gtgagtccta ttatttttt tattaaccct       60 cactaaaggg attttttttt ccagttgagg tggt                                  94

<210> SEQ ID NO 11
<211> LENGTH: 94
<212> TYPE: DNA
<213> ORGANISM: Artificial Sequence
<220> FEATURE:
<223> OTHER INFORMATION: Synthetic Construct

<400> SEQUENCE: 11
ggaagcgcac cttgttttt tttccctata gtgagtccta ttatttttt ttatttaggt       60 gacactatag ttttttttt attctgctgc tcca                                   94
```

ROLLING CIRCLE AMPLIFICATION DETECTION OF RNA AND DNA

RELATED APPLICATION

This application claims the benefit under 35 U.S.C. §119 (e) of U.S. provisional patent application No. 60/257,216, filed Dec. 20, 2000, which is hereby incorporated by reference in its entirety.

The United States Government has rights in this invention pursuant to contract No. W-7405-ENG-48 between the U.S. Department of Energy and the University of California, for the operation of Lawrence Livermore National Laboratory; NIH grant CA55861 and DOE Grant KP110202.

FIELD OF THE INVENTION

This invention relates to the detection of DNA and RNA. In particular, this invention relates to the detection of DNA and mRNA expression levels using rolling circle amplification.

BACKGROUND OF THE INVENTION

Rolling circle amplification (RCA) is a nucleic amplification technique used with a 'padlock' oligonucleotide probe to detect single base changes in isolated nucleic acids (1–5). (Full citations for the references numerically identified herein are given before the claims.) While RCA is a powerful technique in theory, in practice it suffers from sensitivity and reproducibility problems.

Application of RCA to in situ targets in fixed or permeabilized cells has not been uniformly successful to date. Whereas recent work has demonstrated that the concept is viable (8), DNA detection efficiencies of 20–30% lessen the utility of RCA as an assay. Lack of success has been attributed to possible blocking of the polymerase by the target strand, and it was suggested that this problem might be overcome by cutting the target DNA strand near the RCA probe's hybridization site (5). Under these conditions, DNA polymerase could free the probe from the target, in effect spinning the probe away from the target, keeping the polymerase from being blocked during the amplification process. However, this technique did not provide satisfactory results. Numerous attempts to achieve consistent in situ RCA have been made, mostly centered on the development of polymerases that can overcome the problems of stearic hindrance resulting from the RCA procedure. None have been successful; a pair of articles in Nature Genetics [2, 3] describes the necessity for and several possible solutions to in situ RCA, but neither demonstrates the process.

There is thus a need for improved RCA techniques. In particular, there is a need for improved in situ RCA techniques.

SUMMARY OF THE INVENTION

In order to meet these needs, the present invention is directed to improved RCA techniques for the detection of DNA and RNA. In particular, the present invention is directed to improved RCA in situ techniques for the detection of DNA and RNA.

In particular, the present invention is directed to the finding that in addition to restriction enzyme digestion of DNA, additional steps are required to achieve consistent and satisfactory results for RCA detection of DNA, particularly in situ DNA detection. Whereas heat denaturation is typically used to render the target DNA single stranded, the present invention is directed to the finding that complete removal of the non-targeted DNA strand by digestion with exonuclease significantly increases the efficiency of the RCA DNA detection process both in solution and in situ.

The present invention is also directed to the use of RCA to detect mRNA in situ. Using appropriate image analysis techniques, the RCA assay is sufficiently quantitative to enable transcriptionally-mediated dose-response curves to be generated.

Rolling circle amplification (RCA) is a versatile technology used to locate single-base substitutions in DNA and RNA which has proven to be very useful in detecting point mutations in extracellular nucleic acid but has not as yet been successful at detecting base changes in situ. This invention is also directed to a method of employing RCA in situ to detect gene copy number, single base mutations and gene expression levels in individual cultured cells and in tissue sections. By pre-treating DNA with a restriction enzyme and an exonuclease, one strand of the DNA helix is removed. This produces a single-stranded nucleic acid template in which minimal DNA-induced stearic hindrance exists to inhibit the polymerase activity necessary for RCA detection of DNA. The present invention is directed to the use of RCA to detect simultaneously single base changes in genomic DNA and levels of gene expression by amplifying transcribed RNA as well as DNA. When combined with gene isolation and sequencing technologies, the present invention can be used to detect and track mutations in cancer sections, enabling the course of genetic progression to be studied in situ.

The present invention is directed to a method of rolling circle amplification of DNA by: a) providing DNA; b) digesting the DNA with an endonuclease to form nicked DNA; c) digesting the nicked DNA with an exonuclease to prepare the DNA for rolling circle amplification and d) performing rolling circle amplification on the DNA. Such methods can be performed in solution and in situ.

The present invention is further directed to a method of preparing DNA for rolling circle amplification in situ, by a) fixing cells on a surface wherein the cells include DNA; b) digesting the DNA on the surface with an endonuclease to form nicked DNA; and c) digesting the nicked DNA with an exonuclease to prepare the DNA for rolling circle amplification.

In one format, the invention is directed to a method of performing rolling circle amplification in situ, by a) fixing cells on a surface wherein the cells include DNA; b) digesting the DNA on the surface with an endonuclease to form nicked DNA; c) digesting the nicked DNA with an exonuclease to form target DNA; d) ligating a padlock oligonucleotide probe to the target DNA to form ligated DNA and d) performing rolling circle amplification in situ on the ligated DNA.

In another format, the present invention is directed to a method of performing rolling circle amplification in situ, including: a) providing cells embedded in paraffin wherein the cells contain DNA; b) digesting the DNA in the paraffin with an endonuclease to form nicked DNA; c) digesting the nicked DNA with an exonuclease to form target DNA; d) ligating a padlock oligonucleotide to the target DNA to form ligated DNA; and e) performing rolling circle amplification in situ on the ligated DNA.

In one embodiment, the endonuclease is a restriction endonuclease and. Restriction endonucleases and exonuclease are commercially available from companies such as Promega Corporation, Madison Wis.

In another embodiment, the surface is a microscope slide coverslip or a microscope slide.

In another embodiment, the cells utilized in the method of the invention may be prokaryotic, eukaryotic plants or fungi. The eukaryotic cells may be mammalian including human, reptile, amphibian, avian or plant cells. The prokaryotic cells may be bacterial cells.

In another embodiment, the DNA may be selected from eukaryotic, prokaryotic, viral, chromomosomal, mitochondrial or chloroplast DNA.

In another format, the present invention is directed to a kit for rolling circle amplification, including: a) an exonuclease and b) an endonuclease. The kit may further include RCA reaction buffer. The kit may yet further include an oligonucleotide for RCA.

The present invention is further directed to a method of detecting RNA in situ, including: a) fixing cells on a surface wherein the cells include RNA; performing rolling circle amplification in situ on the RNA to detect the RNA in situ. In one format, the surface is a microscope slide. In another format, the cells are centrifuged onto the microscope slide In another format, the cells are fixed by treatment with alcohol. The preferred alcohol is ethanol.

In another format, the invention is directed to a method for performing rolling circle amplification in situ to detect RNA, including: a) centrifuging cells onto a surface; b) fixing the cells on the surface with ethanol; c) hybridizing a padlock oligonucleotide probe to the RNA to form a DNA-RNA hybrid; d) ligating the oligonucleotide probe to the DNA of the DNA-RNA hybrid to form ligated DNA; e) performing rolling circle amplification on the ligated DNA to form amplified DNA; and f) detecting the amplified RNA by determining the levels of amplified DNA.

BRIEF DESCRIPTION OF THE DRAWINGS

The invention will be better understood by reference to the following Figures in which.

DETAILED DESCRIPTION OF THE INVENTION

Figure 1:
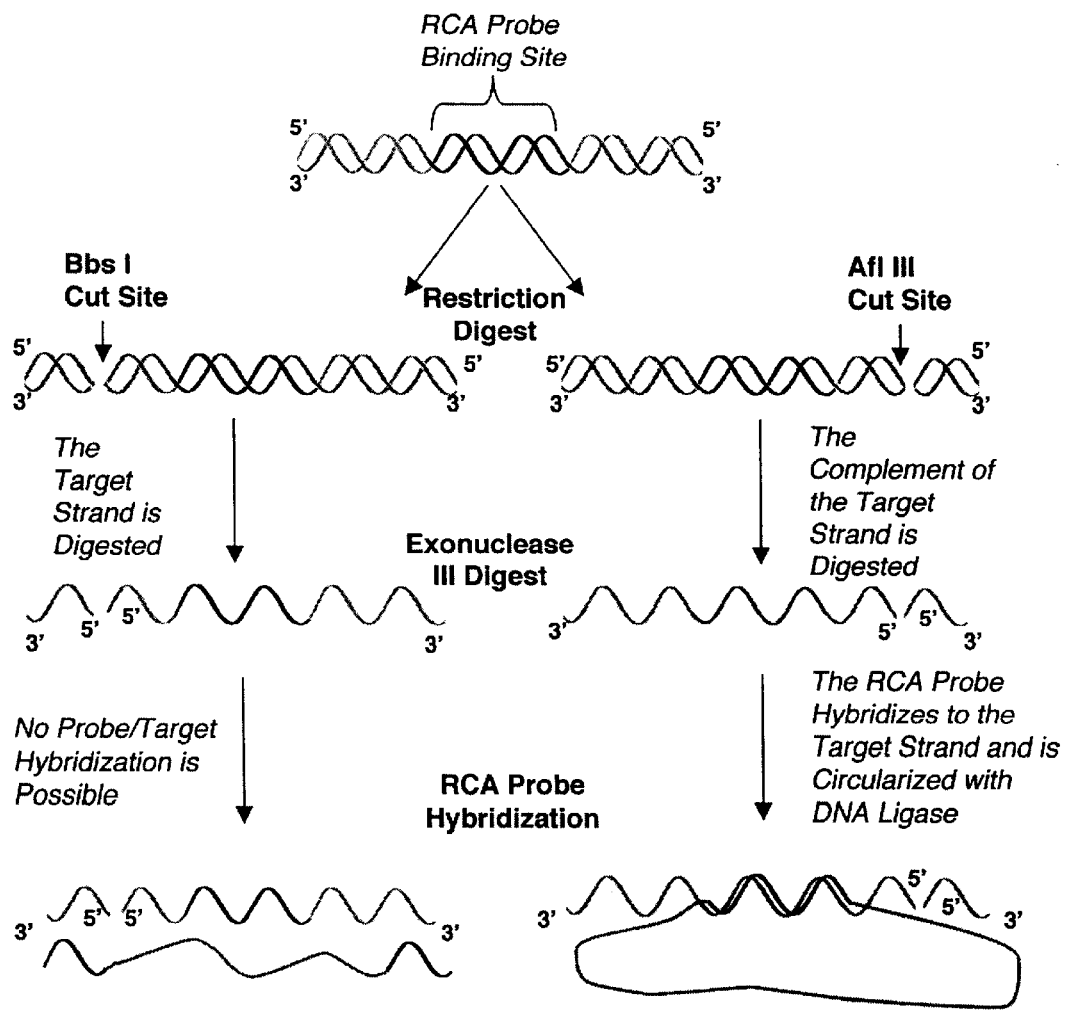
FIG. 1 shows a schematic diagram of rolling circle amplification (RCA) in situ for detection of DNA.

In order to more fully understand the invention, the following definitions are provided.

Rolling Circle Amplification (RCA): Rolling circle amplification (RCA) is a molecular cytogenetic technique used with a 'padlock' oligonucleotide probe to detect single base changes in isolated nucleic acids. At 10 bases per helical turn, the hybridized probe wraps around its target 3 times, and the remaining 70 bases form an unhybridized single-stranded loop. Post-hybridization DNA ligation connects the two ends of the probe in the middle of the 30 base binding region. The unbound 70 base loop facilitates probe circularization and permits approximately 20 bases to serve as a primer recognition site for DNA polymerase to replicate the circle. Rolling circle amplification may be performed in solution or in situ.

Polymerase Chain Reaction (PCR): The polymerase chain reaction (PCR) is a technique utilized to amplify DNA. Typical PCR reactions include appropriate PCR buffers, DNA polymerase and one or more oligonucleotide primers. Various modifications of PCR techniques are possible as detailed in *Current Protocols in Molecular Biology* ed. F. M. Ausubel, R. Brent, D. D. Moore, K. Struhle, Massachusetts General Hospital and Harvard Medical School (1987) which is hereby incorporated by reference.

Oligonucleotide Primers: Oligonucleotide primers (oligos) are short chains of nucleotides useful in RCA techniques, PCR techniques, DNA sequencing and cloning methods as probes. They can be hybridized to DNA or RNA, either in solution or in situ.

Padlock Oligonucleotide Probes: Padlock probes are probes comprised of approximately 100 nucleotides which hybridize to targets of approximately 30 bases and find use in RCA. The 30-base target-binding region of the probe is split into two approximately 15-base segments placed in opposite orientation at each end of the linear probe so that a circle must be formed for hybridization to occur (6, 7).

RCA In Situ: RCA in situ is similar to conventional RCA in solution except that the RCA reaction mix is added to a chromosome template on a surface such as a microscope slide or cover slip or to a formalin-fixed paraffin-embedded tissue section rather than in a microfage tube. With RCA in situ, the RCA products remain closely associated with their target sequences. The reaction products can be identified, if necessary, by incorporating a dNTP-conjugated fluorochrome to the RCA solution.

Endonuclease: An endonuclease is an enzyme that makes a nick in both strands of double stranded DNA. Such endonucleases are available commercially from manufacturers such as Promega Corporation, Madison Wis.

Exonuclease: An exonuclease is an enzyme that digests double stranded DNA from a 3' end or a 5' end leaving a single strand of DNA in its wake. Exemplary but not limiting examples of exonucleases which find use in the invention include 5' exonucleases, 3' exonucleases including Exonuclease III. Such exonucleases are commercially available from manufacturers such as Promega Corporation, Madison Wis.

Taking into account these definitions, the present invention is directed to methods of rolling circle DNA and RNA amplification.

Rolling Circle Amplification

Rolling Circle Amplification (RCA) is a molecular cytogenetic technique used in conjunction with a 'padlock' oligonucleotide probe to locate and detect single base changes in DNA and RNA. The padlock probe is used to locate the individual base, and RCA is used to create a large enough signal to be detectable by conventional microscopy.

Oligonucleotides (oligos) are short linear strands of synthetic DNA that are frequently used as probes. They can be hybridized to DNA or RNA, either in solution or in situ, and are generally detected by fluorescence. The fluorescing of the oligos is achieved by attaching either a fluorescent molecule or an antigen (to which a fluorescently tagged antibody is later attached) directly to the oligo. This works well when the probe is thousands of bases long, but as the length of the probe decreases, the amount of fluorescent label that can be attached to the probe also decreases. This generally limits the length of probe that can be detected to approximately 1000 bases.

Padlock probes were designed to lower this limit of detection [1]. Padlock probes are oligos about 100 bases long, designed to hybridize to a segment of nucleic acid less than half that length, perhaps 30 bases. Of those 30 bases, approximately 15 are represented on one end of the padlock probe and approximately 15 on the other end. Thus, when the padlock probe hybridizes to its target, the probe forms a circle. Due to the fact that DNA is a helix, and makes a full turn every 10 bases, in 30 bases the probe is wrapped around its DNA target 3 times, with the remaining 70 bases forming the unhybridized part of the loop. Post-hybridization treatment with a DNA ligase attaches the two ends of the oligo to one another, in the middle of the 30 base binding segment.

Once the padlock probe is circularized, RCA can be performed. In a padlock probe the 70 base segment of the loop that is not bound to the DNA target may be 'junk' sequence, serving to facilitate circularizing the probe and facilitating primer recognition. Using approximately 20 bases of this loop as a target for a DNA primer (a small oligo such as used to provide the starting point for a PCR reaction) allows a DNA polymerase to begin replicating the circle. An isothermal process, the polymerase progresses continuously around the loop until the 100 base circle has been replicated hundreds or thousands of times. While this serves as an excellent means of detecting small segments of DNA, the padlock probe can be designed to circularize in such a way as to place the gap between the two end bases directly over a particular base on a target. If one wants to determine whether a particular base in a gene has been changed from, for example, guanine to adenosine, one simply makes two nearly identical vectors. One of the two vectors contains the complement to the normal base, and the other contains the complement to the mutated base. If the last base in the oligo is not complementary to the target, it will not hybridize, the padlock will not circularize, the polymerase will not progress continuously around the loop and no fluorescent signal will be detected. Consequently, the 'mutant' oligo will only be detected if it hybridizes completely with the mutant target, and the 'normal' oligo will only be seen if it hybridizes completely with a normal target.

In order to differentiate between the normal and mutant RCA vector products, each RCA oligo also has a short unique sequence incorporated in its non-binding region. Oligos with the same sequences as these sites are included in the reaction mixture; each sequence is labeled with a particular fluorophor (e.g., green for the normal and red for the mutant). As each loop is replicated, the sequence produced is complementary to the original loop, and therefore complementary to that of the labeled oligos. These labeled oligos hybridize to the RCA reaction products from their respective vector, and the 'normal' reaction products turn green and the 'mutant' products turn red.

Thus, the number of targets examined simultaneously is limited only by the number of different fluorophors available. The technology for detecting products resulting from a PCR or other DNA amplification process allows differentiation among multiple targets.

The polymerase is impeded by the interaction of the padlock probe with the target DNA as it replicates the loop. However, this severely limits the effectiveness of RCA. As the polymerase replicates the padlock circle, the target DNA becomes coiled within the ring and physically blocks polymerase activity. This blockage is far greater in fixed cells, in which the DNA is still contained in the chromatin structure. While RCA works well on DNA that has been extracted from cells and purified, it does not been work well in situ.

In Situ RCA

In addition to RCA in solution, performing RCA in fixed cells and tissue sections to detect RNA or DNA is extremely desirable, since it would allow specific mutations to be tracked throughout a diseased tissue, provide information on genetic changes and gene expression involved in initiation and progression of various conditions.

DNA Detection

As a first step in the process of performing DNA RCA in situ, cells and chromosomes are fixed to solid surfaces such as a microscope slide or cover slip by procedures well known in the art. Whole blood is cultured generally for 48 h after which Colcemid is added to arrest the cells in metaphase. Colcemid disrupts the mitotic spindle causing the cells to stop cycling in metaphase. The cultures are then harvested 4 h later by treatment with hypotonic solution such as 0.075 M KCl followed by three fixations in methanol:acetic acid (3:1 v/v). The fixed cells are then dropped onto a solid surface such as 24×60 mm coverslips where they are air dried and stored at room temperature. The fixed cells are generally used within 24 hours of fixation in the procedures of this invention.

The present invention is directed to a means to perform in situ RCA, based on target preparation prior to hybridizing the oligo that allows commercially available DNA polymerases to be used for in situ RCA.

The procedure of the present invention is based on avoiding the use of high processivity enzymes by preparing the target strand more effectively. The article by Nilsson, et al. (8) describes an RCA technique that requires a particular DNA polymerase, from the *Bacillus subtilus* phage $\phi$29 to be successful. Any DNA polymerase with strand displacement ability will work with this invention.

The procedure of the present invention has two steps prior to RCA detection of DNA. These steps are shown in detail in FIG. 1. First, the DNA is nicked with a restriction endonuclease. Second, the double helix is rendered single-stranded by digestion with an exonuclease, for example exonuclease III. Finally, conventional RCA is performed. The two crucial steps are the digestions with the restriction endonuclease and exonuclease III. These steps can be performed in solution or in situ.

Endonuclease Digestion

An endonuclease is an enzyme that makes a nick in both strands of double stranded DNA. The endonuclease digestion is carefully chosen to put a nick in the DNA strand to which the padlock probe will hybridize. Any restriction endonuclease will suffice so long as it is target specific. It is important to make the nick as close as possible to the binding site of the RCA vector without actually being within the vector'binding site. Also, the nick on the strand of DNA to which the vector binds must be 5' to the binding site. Each gene, mutation or region must be predigested by a particular endonuclease that is specifically chosen to make a nick in the appropriate place. Selection or an endonuclease is routine experimental work to one of ordinary skill in the art.

Exonuclease Digestion

An exonuclease is an enzyme that digests double stranded DNA from a 3' end, leaving a single strand of DNA in its wake. For example, Exonuclease III will proceed from a nick in a DNA strand until it comes to a place where the DNA is already single stranded, and then it stops. Since the endonuclease digest makes nicks in both strands of the DNA, the exonuclease will digest both strands at the same time until a series of interlocking single stranded products remain. Careful choice of the restriction endonuclease cutting site as described above results in the target DNA sequence always remaining following exonuclease III digestion.

RCA Hybridization

After digestion, the RCA vector is then hybridized to the DNA template. This template can be, but is not limited to, eukaryotic, prokaryotic, viral, chromomosomal, mitochondrial or chloroplast DNA. Any type of nucleic acid can serve as a target. Hybridization and ligation occur simultaneously; those vectors that are not hybridized to their correct targets will not be ligated. The unbound/unligated target is washed off the slide on which the reaction is being performed. The 'rolling' part of the reaction is done as by procedures well known in the art. Heat stable polymerases find use in the methods of the invention as they allow the reactions to proceed at higher temperatures that are more conducive to target specificity.

RNA Detection

RNA may be detected by RCA in solution, on slides and in paraffin sections. For RNA detection on slides, the slides are generally prepared by centrifuging live cells suspended in phosphate-buffered saline onto glass slides followed by fixation in ethanol for time sufficient to fix the RNA to the slide, generally around 5 minutes. The choice of ethanol appears to be critical as the reaction does not work with methanol or acetic acid. The timing of the fixation step is not critical. The cells prepared for RNA detection by RCA are not treated with restriction enzymes or exonuclease III, nor are they heat denatured. T4 RNA ligase (Epicenter) is used for the ligation of the probes to the RNA. The slides are stained with, e.g. Acridine Orange (AO) at room temperature, rinsed in buffer and sterile water at room temperature, then mounted in buffer and stained with DAPI.

This invention will be better understood by reference to the following non-limiting Example.

EXAMPLE 1

1a. Target Preparation: Two cell lines were used in these experiments. One was a human lymphoblastoid (HLB) line (Coriell Cell Depository) putatively normal with regard to karyotype and gene expression. The other was a Molt-4 lymphoid cell line (available from the American Type Culture Collection) derived from a patient with acute lymphoblastoid leukemia. HLB cells were expected to have two normal copies of the Tp53 gene, and to be normal with regard to Tp53 expression. Molt-4 cells are reported by ATCC to express no normal Tp53, and to have one normal and one or more abnormal copies of the Tp53 gene, in which there is a G->A transition in codon 248 of exon 7. Cells were prepared for DNA detection by first incubating in a hypotonic solution (0.075 M KCl) for 30 min at 37° C. followed by three fixations in methanol:acetic acid (3:1 v/v) and dropped on clean glass microscope slides. Fixed cells on slides were covered with 50 µl of Ribonuclease A (500 µg/mL, Roche) under a glass coverslip. Slides were incubated 1 hr at 37° C. then rinsed with sterile water. Restriction enzymes were used to cut approximately 20 base pairs either 3' or 5' of the sequence of interest, Tp53 in this case. Either Afl III or Bbs I (0.1 U/µl, New England Biolabs Inc.) were applied for 12 hours at 37° C. Cells were treated with Exonuclease III (1.3U/µl, Life Technologies) in 1×exonuclease III Buffer (50 mM Tris, pH 8.0, 5 mM MgCl$_2$, 1 mM DTT), then incubated 1 hr at 37° C. and rinsed with sterile water.

1b. Single Color Reaction: Simultaneous hybridization and ligation were performed with 0.8 µM of probe, 20 U Ampligase Thermostable DNA Ligase (0.43 U/µl, Epicenter Technologies) and 1×Ampligase buffer. The 50 µl reaction was placed on the slide, covered with a glass coverslip and sealed with rubber cement. The slide was heated to 94° C. for 10 minutes to ensure that both probe and target DNA were single stranded, and then lowered to 42° C. for 1 hour to allow hybridization and ligation of the probe. Slides were washed in 2×SSC at 42° C. for 15 minutes, rinsed in sterile water and blown dry. The RCA reaction mixture consisted of 4µM of T7 primer, 200 µM of each DNTP(Roche), either 63 nM digoxigenin-11-dUTP (Roche) or 63 nM biotin-dUTP (Roche), 2 Units ThermoSequenase DNA Polymerase with Pyrophosphatase (USB) and 1×ThermoSequenase buffer which was added to the slide which was then covered with a coverslip, sealed with rubber cement and heated 12 hr at 54° C. Slides were washed in 2×SSC at 45° C. for 5 minutes, 1×PBS at 45° C. for 5 minutes and rinsed in sterile water at room temperature. Anti-digoxigenin-fluorescein antibody or Texas Red Avidin (Roche, 200 ng/µl) was incubated on the slide at 37° C. for 10 minutes and washed 2×5 min in 1×PBS at room temperature. Slides were mounted in 4',6'-diamido-2-phenylindole (DAPI) in anti-fade and viewed with an Axiophot Fluorescence Microscope (Zeiss).

1c. Dual color reaction: Two probes were used, one complementary to the normal Tp53 gene and the other complementary to the mutated form found in the Molt-4 cells. Each probe was primed with the T7 oligonucleotide, (TAATACGACTCACTATAGGG) [SEQ ID NO:1] and also contained a separate promoter sequence used to hybridize a fluorochrome-tailed oligonucleotide included in the reaction to its complementary amplified sequence. The SP6 promoter (ATTTAGGTGACACTATAG) [SEQ ID NO:2] was used to bind to the reaction products from the mutant probe, GTTCATGCCGCCCttttttttTATTTAG-GTGACACTATAGttttttttCCCTATAGTGAGT CGTATTAttttttttGGTGAGGATGGGCCTCT) [SEQ ID NO:3] and the T3 promoter (ATTAACCCTCACTAAAG) [SEQ ID NO:4] was used to bind to the reaction products of the normal probe GGTTCATGCCGCCCttttttttATTAAC-CCTCACTAAAGGGAttttttttCCCTATAGTGA GTCGTATTAttttftttGGTGAGGATGGGCCTCC), [SEQ ID NO: 5]. Thymidines are used as spacers in the SP6 and T3 sequences and are indicated by lower-case letters. The procedure for ligation and rolling circle amplification are similar to the procedure for a single color reaction. Differences include ligating 0.4 µM of each probe (mutated and normal) as well as incorporating 10 µM of fluorochrome tailed oligonocleotide (T3 and SP6) in place of digoxigenin-dUTP in the RCA reaction. The tailed oligonucleotides were used to obtain different colors for the mutant and normal Tp53 gene sequences. Fluorochrome tailing was achieved with a 10 µM solution of the promoter oligonucleotide with digoxigenin-dUTP (T3 oligo) or biotin-dUTP (SP6 oligo) (100 nM, Roche) using Terminal Deoxynucleotidyl Transferase (1.5 µl, Life Technologies), and 1×Terminal Deoxynucleotidyl Transferase buffer. The reaction was incubated 1 hr at 37° C. .

RNA Detection

2a. Qualitative Detection: RCA using the human Tp53 mRNA complementary probe (CGGTTCATGCCGCCCtt-ttttttttCCCTATAGTGAGTCGTATTAttttttttAGGGAAATCA CTCCCAATTAttttttttGGTGAGGATGGGCCTC) [SEQ ID NO:6] was performed, and digoxigenin-dUTP was incorporated during the reaction. Slides were incubated with fluorescein-conjugated anti-digoxigenin antibody as described. All slides were prepared by centrifuging live cells suspended in phosphate-buffered saline onto glass slides followed by fixation in 100% ethanol for 5 minutes. The cells prepared for this experiment were not treated with restriction enzymes or exonuclease III, nor were they heat denatured. Consequently, no nuclear DNA signal was evident. T4 RNA ligase (Epicenter, 20 Units) was used for the ligation under identical conditions as described above. The slides were stained for 3 minutes with 10 μg/ml Acridine Orange (AO), rinsed in buffer and sterile water at room temperature, then mounted in buffer and stained with DAPI.

2b. Quantitative Detection: Probe sequences for the RNA detection were:

keratin 10,

TGTGAGAGCTGCACAttttttttCCCTATAGTGAGTCCTATTAttttttttTATTTAGGTG

ACACTATAGttttttttATCTGGGCCTGAATC [SEQ ID NO: 7];

GSTT2,

CATTCTTCTTGGCGAttttttttCCCTATAGTGAGTCCTATTAttttttttATTAACCCTC

ACTAAAGGGAttttttttctctaaggggatgc [SEQ ID NO: 8];

Chromosome 18 alpha satellite,

GAATTGAACCACCGTAttttttCCCTATAGTGAGTGAGTCGTATTAtttttAAATATC

ATCTTTGGTGTTTCCTAttttttttGTACTCACACTAAGA [SEQ ID NO: 9];

Tp53, see section 2a above; p72,

GCTACTAGCTCCATttttttttCCCTATAGTGAGTCCTATTAttttttttATTAACCCTCA

CTAAAGGGAttttttttCCAGTTGAGGTGGT [SEQ ID NO: 10];

vimentin,

GGAAGCGCACCTTGttttttttCCCTATAGTGAGTCCTATTAttttttttTATTTAGGTGA

CACTATAGttttttttTATTCTGCTGCTCCA [SEQ ID NO: 11].

All reactions were carried out as described in Section 2a above. Irradiations were carried out in a J. L. Shepherd and Associates Mark 1 137 Cs source. Pixel intensities for each image were established using Scanalytics' IPLabs Scientific Imaging software.

To detect the Tp53 gene in HLB cells, cells were fixed on slides and treated with two nucleases prior to RCA (FIG. 1).

FIG. 1 shows a flow diagram of DNA RCA in situ. Pretreatment prior to in situ RCA detection of the Tp53 gene is required. Restriction enzymes were used to cut approximately 20 base pairs either 3' or 5' of the probe binding site. Afl III was used for digestion 5' of the binding site, and Bbs I was used for digestion 3' of the target. Cells were then treated with Exonuclease III, which digests DNA 3'-5' starting with 3' hydroxyl left by the endonuclease, resulting in staggered single stranded DNA. The DNA strand remaining following Afl III digestion in this case is the complement to the 'sense' probe sequence. DNA remaining following BbsI digestion is the complement to the 'antisense' probe sequence. Bbs I digestion constitutes a negative control for the RCA process using the sense probe, and Afl III constitutes a negative control for the antisense probe. The two ends of the sense probe create an incomplete circle as they anneal to the complementary site on the DNA digested with Bbs I. The DNA strand digested with Afl III is complementary to the sense probe and allows it to anneal and ligate, completing the circle and locking the probe onto the target. Targets other than Tp53 may require different endonucleases.

DNA was cut with a restriction endonuclease, then the double helix was rendered single-stranded by digestion with exonuclease III. Padlock probe hybridization and RCA followed. Endonuclease digestion was carefully selected to place a cut within approximately 20 bases of the probe's binding site but without actually being within that site. The substrate for Exonuclease III is double-stranded DNA, which it digests from a 3' end leaving a single strand of DNA in its wake, proceeding until it reaches a region where the DNA is already single stranded (9, 10). Thus, the entire genome will still be represented following exonuclease digestion, but for any given locus only one of the two strands will be present.

Success of the RCA reaction depended on the probe's target sequence remaining intact following digestion. To ensure that the target strand was not removed by the exonuclease treatment, the endonuclease had to cut 5' of the site on the strand to which the probe bound, and a second cut must not occur too near the 3' end on the target strand. Identical RCA reactions were performed with two probes that were complementary to the Tp53 gene present in two copies in the target cells. One of the probes was complementary to the coding strand, the other to the non-coding strand. In one set of reactions the target strand was cut 3' to the binding site, and in the other set the cut was 5' to the site. Each reaction was carried out using either the probe complementary to the transcribed strand or the probe complementary to the non-transcribed strand; only one probe was present in each reaction. Reaction products were labeled by incorporating a hapten-conjugated nucleotide (either biotin or digoxigenin) in the reaction mixture. The results were detected by a subsequent treatment with a fluorochrome-conjugated (Texas Red or fluorescein) antibody to the hapten, producing fluorescent labeled signals at the site of the reaction. In every test, reactions with 5' nicks successfully produced labeled signals whereas reactions with nicks 3' to the target never produced signals.

Figure 2:
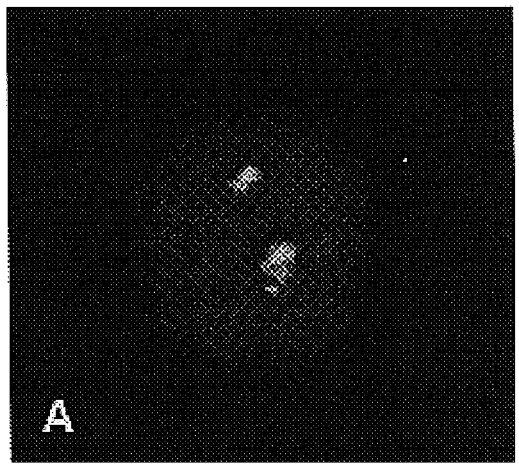
FIG. 2 shows the use of RCA in Human Lymphoblastoid (HLB) cells in the presence of digoxigenin-dUTP(A) or biotin-dUTP(B) for copy number detection.
Figure 2:
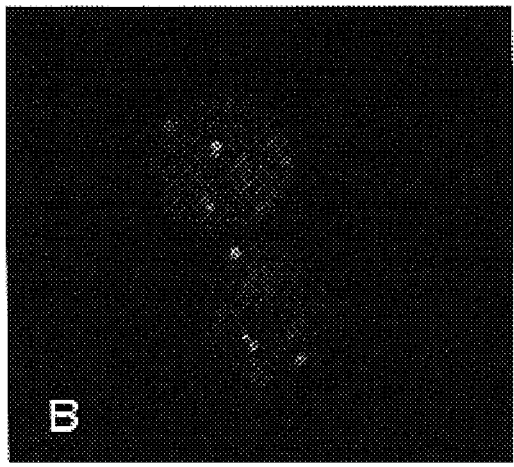

To determine gene copy number, RCA using the Tp53 probe was performed on methanol:acetic acid (3:1)-fixed cells on glass slides subsequently treated with enzymes as described above. We scored 200 interphase cells for the number of fluorescent signals present, with the criteria that two labeled spots indicated a normal cell and 3 or more spots indicated aneuploidy (FIG. 2). FIG. 2 shows copy number detection in RCA in HLB cells in the presence of digoxigenin-dUTP (A) or biotin-dUTP (B) unambiguously identifies very short DNA sequences in the Tp53 gene. In (B), both normal and aneuploid cells are evident, consistent with their known karyotypic variability.

Approximately 10% of the cells that were scored showed 1 or no spots; we counted these as failed in reaction. Of the cells that showed 2 or more signals, 6% showed 3 or more (scored as aneuploid) while 94% had 2 signals. Scoring metaphase chromosomes showed a 5% aneuploid rate; these HLB cells are known to develop a small degree of aneuploidy in culture, but are generally considered to be 'normal' non-primary cell lines. We repeated these studies using probes for other genes, and for an alpha satellite repeat, and obtained similar results (not shown). We also tested the notion that it was the breaks in the target strand rather than the single stranded target that was responsible for increasing the efficiency of RCA. Treating only with a restriction enzyme, and not with exonuclease III, produced no significant increase in efficiency over only heat denaturation and no enzymatic treatment at all. We also studied other ways of rendering target DNA single stranded. Simply cutting the target DNA with restriction enzymes produced no signal at all, and following the restriction enzyme treatment with heat denaturation produced efficiencies of approximately 25%. Thus, rendering the target DNA unifilar at the binding site appears to be responsible for increasing the detection efficiency of RCA.

To demonstrate the application of RCA in detecting single base changes in nucleic acid targets in situ, Molt-4 cells were examined. Two separate probes complementary to a 30 base region of this exon were constructed. One probe contained the complement to the normal base, and the other the complement to the mutant base with the 3' terminal base of each probe corresponding to the site of the mutation. If the terminal base in the probe is not complementary to the target, that base will not hybridize, preventing ligation and blocking the polymerase from progressing continuously around the loop with the result that no fluorescent signal will be generated. Consequently, the mutant and normal target sequences will only be detected by their respective probes. To differentiate between the reaction products the sequences of two bacteriophage promoters were incorporated into the RCA probes. Because the T7 promoter primer is incorporated into the probes to initiate the RCA reaction, we incorporated either the T3 (for the normal sequence probe) or SP6 (for the mutant sequence probe) bacteriophage promoter sequences into the RCA probes. Oligomers corresponding to the two promoter sequences were then included in the RCA reaction and were differentially labeled, T3 with digoxigenin and SP6 with biotin. During the RCA reaction, each replication of the probe produces a single stranded sequence complementary to the promoter sequence contained within the probe. The T3 or SP6 oligomers should hybridize to these sites as they are produced, labeling each product with either digoxigenin or biotin. Amplification products of Tp53 in Molt-4 cells were detected using a fluorescein-conjugated anti-digoxigenin antibody and Texas Red-conjugated avidin to produce green and red signals at the sites of the normal and mutant alleles, respectively (FIG. 3).

Figure 3:
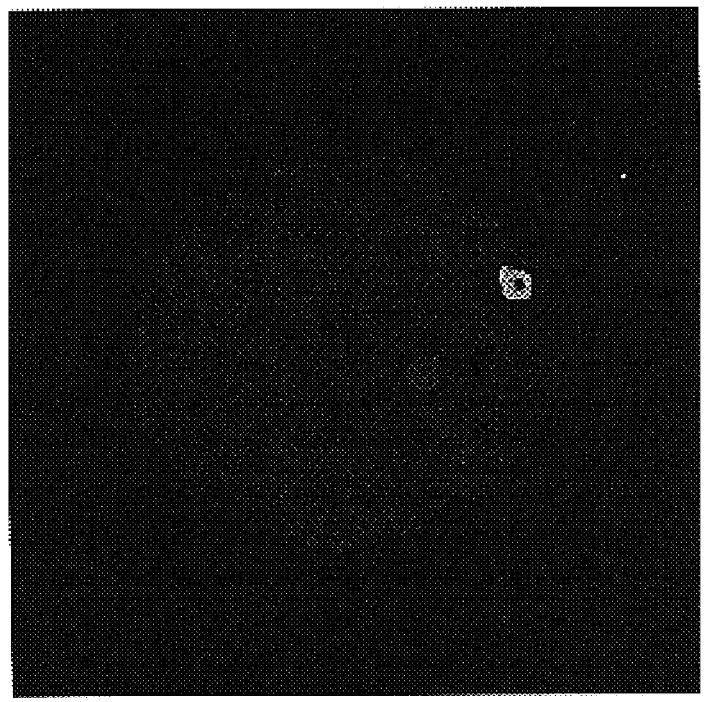
FIG. 3 shows a Molt-4 cell in which a single nucleotide (G to A) difference in two alleles of the Tp53 gene was detected by RCA in situ.

FIG. 3 shows allele discrimination in a Molt-4 cell in which a single nucleotide (G to A) difference in two alleles of the Tp53 gene was detected by RCA in situ as discussed above. Two probes were used, which differed in that the 3' terminus of the normal and the mutant versions were complementary to the normal (green signal) and the mutant (red signal) sequences, respectively.

It is important to note that the binding sequences of the mutant-complement and normal-complement probes differ by only a single base. Whereas this difference is placed so as to prohibit the two ends of the probe from being ligated and amplified should they anneal to the incorrect site (mutant to normal site or the reverse), it is insufficient to stop such mis-binding from occurring at all loci. Some fraction of the time, this mis-hybridization will occur, and while improperly-bound probe will be washed away prior to amplification, no signal will be produced at that site. Thus, for simultaneous 2-probe binding, to prevent such false negatives each probe should be hybridized, ligated and washed off sequentially. The wash step will not remove properly bound and ligated probe, but it will remove unligated material. This process will ensure the maximum possible efficiency of detection. Even with this precaution, efficiencies for two color detection were considerably lower than for single color RCA (approximately 30% as compared to greater than 90%). We attribute this to the method of fluorescence labeling, as it is similarly inefficient when used for only single color detection.

By designing an RCA probe's binding site to be complementary to a transcribed mRNA sequence, gene expression could also be detected. The method of cell fixation for RNA detection was considerably more important than for DNA detection. Although various methods of cell preparation, including conventional acid:alcohol fixation and alcohol fixation yielded similar results for DNA-based RCA in situ, routine detection of RNA was made possible by centrifuging the cells onto slides in culture media followed by an alcohol wash. In these experiments, a probe with a 30 base binding site complementary to a transcribed region of the Tp53 gene was used to determine the presence of Tp53 mRNA in Molt-4 and HLB cell lines. Unlike HLB cells, Molt-4 cells produce no normal Tp53 transcripts (11). Single-color RCA was performed both before and after treatment of fixed cells with RNase. HLB and Molt-4 cells were also stained with Acridine Orange (AO) following all treatments prior to the RCA step to ensure that the results of the RCA reaction corresponded with the actual status of RNA in the cells. In each case, AO staining detected RNA prior to, but never following, RNase treatment. RCA performed on HLB cells that had not been treated with RNase showed considerable labeling in the cytoplasmic region surrounding the nucleus (FIG. 4).

Figure 4:
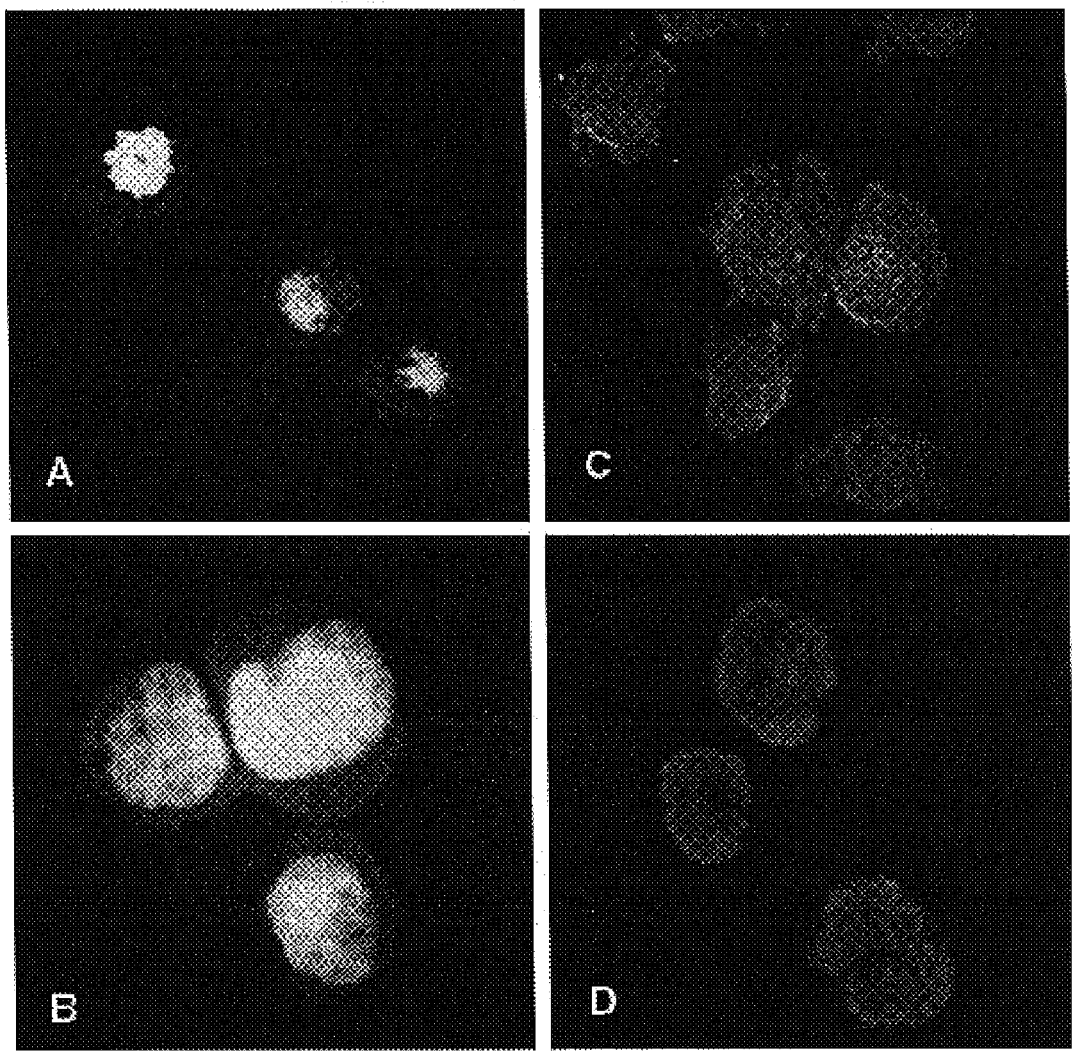
FIG. 4 shows mRNA detection in normal HLB cells(A) and Molt-4 cells(B) stained with acridine orange.

FIG. 4 shows mRNA detection in normal HLB cells (A) and Molt-4 cells (B) stained with Acridine Orange (AO), which labels single stranded nucleic acid (RNA) red and double stranded nucleic acid (nuclear DNA) yellow. Panels A and B demonstrate the presence of RNA in each of the cell types. RCA was performed on replicate cell preparations using a probe with 3' and 5' DNA binding site complementary to the probe described in FIG. 3.(C) The green fluorescence signal surrounding the nuclei of the HLB cells demonstrates the presence of Tp53 transcript detected by RCA. (D) No such signal is seen in the Molt-4 cells, demonstrating the lack of normal Tp53 transcript. In the Molt-4 cells, however, no RCA products were detected whether the reaction was performed pre-or post-RNase. In the HLB cells, only the post-RNase treated RCA reaction was null. As an additional control, an RCA probe with a binding site that was a copy of the Tp53 mRNA, rather than a complement to it, was tested and produced no signal.

RCA probes were constructed to bind to the mRNA of several genes known to be radiation dose responsiveas shown at the web site rex.nci.nih.gov/RESEARCH/basic/lbc/patent/web6kinduced including Tp53, human DEAD-box protein p72, vimentin, keratin 10 and glutathione S-transferase theta 2 (GSTT2). HLB cells were exposed to 137 Cs gamma rays at doses up to 2 Gy, then fixed and evaluated by RCA. For each RCA probe, three different ligases were used: Ampligase, T4 DNA ligase and T4 RNA ligase, the latter of which has been reported as an effective ligating agent for short DNA fragments (12). All produced similar results, but the T4 RNA ligase products had the highest signal to background ratio. It is important to note that RNA serves only as a hybridization template for the DNA ligase, and that only DNA is ligated, not RNA. Use of DNA ligases to join single stranded fragments of DNA hybridized to an RNA target has been described in the literature (13). As a negative control, each RCA reaction was also run without ligase, the results of which were used to normalize the results of the experiments. A probe complementary to untranscribed alpha satellite DNA was used as an additional negative control. Neither negative control produced a response signal; results are shown in FIG. 5.

Figure 5:
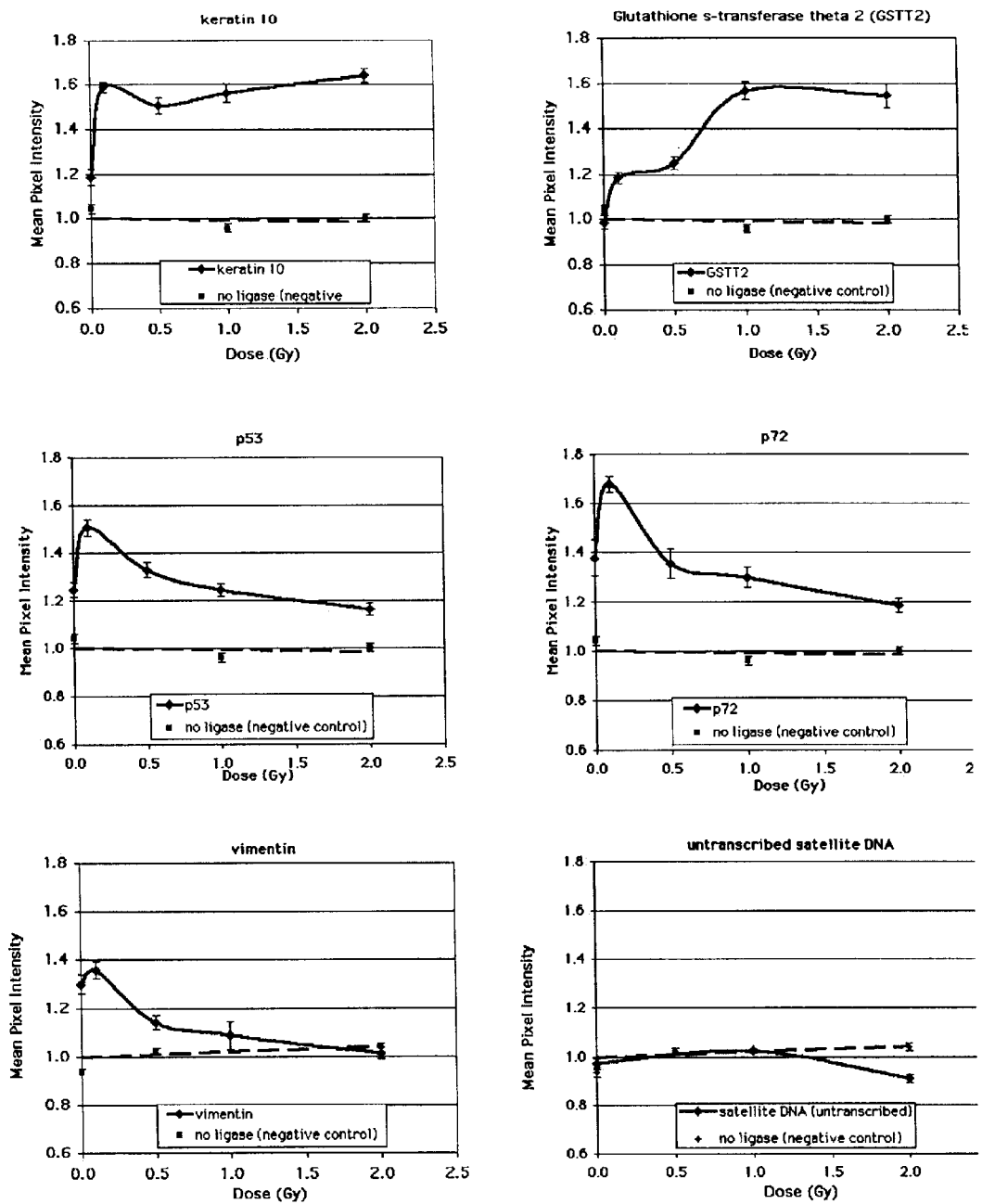
FIG. 5 shows radiation dose response curves of HLB cells.

FIG. 5 shows radiation dose response curves for normal HLB cells that were irradiated, left in culture medium for 2 hours, and then fixed and analyzed. T4 RNA ligase (20 U in 4 μl 10×buffer, Epicentre Technologies) was used to ligate the probes. Each experiment was replicated from a new stock of frozen cells, and produced curves of the same shapes. Fifty to 150 cells were analyzed per data point; error bars represent +/-SEM. Cells were analyzed by measuring mean pixel intensity of green fluorescence using IPLabs image analysis software (Scanalytics Inc.).

The fact that cell lines are frequently unique in their gene expression patterns makes comparison with the literature difficult, but curve shapes for Tp53 and p72 expression in HLB cell lines were confirmed by microarray analysis using the Affymetrix array system [14].

We have shown that RCA in situ is useful for discriminating alleles, determining gene copy number, and quantifying gene expression in single cells. The sensitivity, specificity and speed of RCA may also allow it to be used for focused investigations of cell and tissue responses to drugs of pharmaceutical importance, for evaluation of adverse environmental exposure to humans by ionizing radiation and chemicals, and for clinical purposes such as prenatal diagnosis and pathological characterization of tumors. The exquisite sensitivity of in situ RCA may add an entirely new dimension to the fields of genomics, pathology, mutagenesis and cytogenetics.

References

The following references referred to numerically in the specification are hereby incorporated by reference in their entirety:

1. Baner, J., Nilsson, M., Mendel-Hartvig, M. and Landegren, U. (1998) Nucleic Acids Res, 26, 5073–5078.
2. Schweitzer, B., Wiltshire, S., Lambert, J., O'Malley, S., Kukanskis, K., Zhu, Z., Kingsmore, S. F., Lizardi, P. M. and Ward, D. C. (2000) Proc Natl Acad Sci U S A, 97, 10113–10119.
3. Lizardi, P. M., Huang, X., Zhu, Z., Bray-Ward, P., Thomas, D. C. and Ward, D. C.(1998) Nat Genet, 19, 225–232.
4. Lizardi, P. M. and Ward, D. C. (1997) Nat Genet, 16, 217–218.
5. Thomas, D. C., Nardone, G. A. and Randall, S. K. (1999) Arch Pathol Lab Med, 123,1170–1176.
6. Nilsson, M., Antson, D. O., Barbany, G. and Landegren, U. (2001) Nucleic Acids Res, 29, 578–581.
7. Nilsson, M., Krejci, K., Koch, J., Kwiatkowski, M., Gustavsson, P. and Landegren, U. (1997) Nat Genet, 16, 252–255.
8. Nilsson, M., Malmgren, H., Samiotaki, M., Kwiatkowski, M., Chowdhary, B. P. and Landegren, U. (1994) Science, 265, 2085–2088.
9. Rodrigues, N. R., Rowan, A., Smith, M. E., Kerr, I. B., Bodmer, W. F., Gannon, J. V. and Lane, D. P. (1990) Proc Natl Acad Sci U S A, 87, 7555–7559.
10. Goodwin, E. and Meyne, J. (1993) Cytogenet Cell Genet, 63, 126–127.
11. Meyne, J. and Goodwin, E. H. (1994) Methods Mol Biol, 33, 141–145.
12. Troutt, A. B., McHeyzer-Williams, M. G., Pulendran, B. and Nossal, G. J. (1992) Proc Natl Acad Sci U S A, 89, 9823–9825.
13. Zhong, X. B., Lizardi, P. M., Huang, X. H., Bray-Ward, P. L. and Ward, D. C. (2001) Proc Natl Acad Sci U S A, 98, 3940–3945.

What is claimed is:

1. A method of rolling circle amplification of DNA comprising:
   a) providing DNA;
   b) digesting said DNA with an endonuclease to form nicked DNA;
   c) digesting said nicked DNA with an exonuclease to prepare exonuclease-treated DNA for rolling circle amplification; and
   d) performing rolling circle amplification on said exonuclease-treated DNA.

2. The method of claim 1 wherein said endonuclease is a restriction endonuclease.

3. The method of claim 1 wherein said exonuclease is exonuclease III.

4. The method of claim 1 wherein said DNA is provided from cells selected from the group consisting of bacterial, mammalian, reptile, amphibian, avian and plant cells.

5. The method of claim 4 wherein the cells are mammalian cells.

6. The method of claim 5 wherein the mammalian cells are human cells.

7. A method of preparing DNA for rolling circle amplification in situ, comprising:
   a) fixing cells on a surface wherein said cells comprise DNA;
   b) digesting said DNA on said surface with an endonuclease to form nicked DNA; and
   c) digesting said nicked DNA with an exonuclease to prepare said DNA for rolling circle amplification.

8. The method of claim 7 wherein said endonuclease is a restriction endonuclease.

9. The method of claim 7 wherein said surface is a microscope slide.

10. The method of claim 7 wherein said surface is a microscope slide coverslip.

11. The method of claim 7 wherein said exonuclease is exonuclease III.

12. The method of claim 7 wherein the cells are selected from the group consisting of bacterial, mammalian, reptile, amphibian, avian and plant cells.

13. The method of claim 7 wherein said mammalian cells are human cells.

14. The method of claim 7 wherein said DNA is selected from the group consisting of eukaryotic, prokaryotic, viral, chromosomal, mitochondrial and chloroplast DNA.

15. A method of performing rolling circle amplification in situ, comprising:
   a) fixing cells on a surface wherein said cells comprise DNA;
   b) digesting said DNA on said surface with an endonuclease to form nicked DNA;
   c) digesting said nicked DNA with an exonuclease to form target DNA;
   d) ligating a padlock oligonucleotide probe to said target DNA to form ligated DNA; and
   e) performing rolling circle amplification in situ on said ligated DNA.

16. The method of claim 15 wherein said endonuclease is a restriction endonuclease.

17. The method of claim 15 wherein said surface is a microscope slide.

18. The method of claim 15 wherein said surface is a microscope slide coverslip.

19. The method of claim 15 wherein said exonuclease is exonuclease III.

20. The method of claim 15 wherein the cells are selected from bacterial, mammalian, reptile, amphibian, avian and plant cells.

21. The method of claim 20 wherein said mammalian cells are human cells.

22. The method of claim 15 wherein said DNA is selected from the group consisting of eukaryotic, prokaryotic, viral, chromosomal mitochondrial and chloroplast DNA.

23. A method of performing rolling circle amplification in situ, comprising:
   a) providing cells embedded in paraffin wherein said cells comprise DNA;
   b) digesting said DNA in said paraffin with an endonuclease to form nicked DNA;
   c) digesting said nicked DNA with an exonuclease to form target DNA;
   d) ligating a padlock oligonucleotide to said target DNA to form ligated DNA; and
   e) performing rolling circle amplification in situ on said ligated DNA.

24. The method of claim 23 wherein said endonuclease is a restriction endonuclease.

25. The method of claim 23 wherein said exonuclease is exonuclease III.

26. The method of claim 23 wherein the cells are selected from the group consisting of bacterial, mammalian, reptile, amphibian, avian and plant cells.

27. The method of claim 26 wherein said mammalian cells are human cells.

28. The method of claim 23 wherein said DNA is selected from the group consisting of eukaryotic, prokaryotic, viral, chrommomosomal, mitochondrial and chloroplast DNA.

29. A method of detecting RNA in situ, comprising;
   a) fixing cells on a surface with ethanol wherein said cells comprise RNA; and
   b) performing rolling circle amplification in situ on said RNA to detect said RNA in situ.

30. The method of claim 29 wherein said surface is a microscope slide.

31. The method of claim 29 wherein said cells are centrifuged onto said microscope slide.

32. The method of claim 31 wherein said cells are fixed with ethanol for 5 minutes.

33. A method for performing rolling circle amplification in situ to detect RNA, comprising:
   a) centrifuging cells onto a surface;
   b) fixing said cells on said surface with ethanol;
   c) hybridizing a padlock oligonucleotide probe to said RNA to form a DNA-RNA hybrid;
   d) ligating said oligonucleotide probe to said DNA of said DNA-RNA hybrid to form ligated DNA;
   e) performing,rolling circle amplification on said ligated DNA to form amplified DNA; and
   f) detecting said amplified RNA by determining the levels of said amplified DNA.

34. The method of claim 33 wherein said surface is a microscope slide.

35. The method of claim 33 wherein said cells are fixed with ethanol for 5 minutes.

* * * * *